United States Patent
Pedack

Patent Number: 5,838,421
Date of Patent: Nov. 17, 1998

[54] BINOCULAR DIRECT OPTHALMOSCOPE

[76] Inventor: Henry Pedack, 3228 Iowa Dr., Bellingham, Wash. 98226

[21] Appl. No.: 825,742

[22] Filed: Apr. 3, 1997

[51] Int. Cl.$^6$ ....................................................... A61B 3/10
[52] U.S. Cl. ........................... 351/218; 351/221; 351/245
[58] Field of Search ................................... 351/205, 218, 351/221, 245, 244

[56] References Cited

U.S. PATENT DOCUMENTS

| | | | |
|---|---|---|---|
| 3,315,680 | 4/1967 | Silbertrust et al. | 606/4 |
| 3,783,874 | 1/1974 | Koester et al. | 606/4 |
| 3,984,157 | 10/1976 | Le Vantine | 351/221 |
| 4,461,551 | 7/1984 | Blaha | 351/221 |
| 4,711,540 | 12/1987 | Yoshino et al. | 351/214 |
| 4,836,188 | 6/1989 | Berry | 128/6 |
| 5,078,469 | 6/1992 | Clark et al. | 359/481 |
| 5,302,988 | 4/1994 | Nanjo | 351/221 |

*Primary Examiner*—Huy Mai
*Attorney, Agent, or Firm*—Brian J. Coyne

[57] ABSTRACT

A portable, binocular direct ophthalmoscope. A frame carrying a binocular optical system is suspended for rotation about a pivot axis from one end of a support beam; an opposite end of the support beam is attached to a handle. A beam splitter block mounted to the frame carries an illumination source for light emission along an illumination axis and into an eye of a subject. Left and right beam splitting mirrors attached to the block are symmetrically and obliquely disposed on opposite sides of the illumination axis. Light reflected back from the subject's eye is split by the beam splitting mirrors into a left-directed beam and a right-directed beam, which are each reflected rearward by laterally spaced apart deflection mirrors through left and right dioptric disk assemblies and thence into the left and right eyes of an observer, respectively. This arrangement permits positioning the light source and the beam splitting mirrors all within a circle normal to the illumination axis of diameter no more than 6 to 7 mm, thereby achieving a stereoscopic image. In a first embodiment of the invention, the dioptric disk assemblies are attached to mounts that slide within a C-channel attached to the frame for adjustment to the interpupillary distance of the observer. In a second embodiment, worm gear assemblies interconnected by a telescopic coupling rotate dioptric disks when attached lens power knobs are turned. In a third embodiment, a pair of laterally adjustable dioptric disks are provided with radial teeth that engage the teeth of an idler gear.

9 Claims, 11 Drawing Sheets

BINOCULAR DIRECT OPTHALMOSCOPE

BACKGROUND OF THE INVENTION

1. Field of the Invention

The present invention pertains generally to ophthalmoscopes, and more particularly to a portable, hand-held, binocular ophthalmoscope capable of both direct and indirect stereoscopic viewing of the interior of an eye through the pupil.

2. Background Art

The monocular ophthalmoscope was invented in 1851 by a German physicist, Hermann von Helmholtz. It was an optical instrument for viewing the inner eye of a subject, comprising a light source, an apertured, concave mirror for reflecting light from the source toward the subject's eye, and magnifying lenses for interposition between an eye of an observer and light reflected back from the interior of the subject's eye through the aperture in the mirror. In its modern form, the monocular ophthalmoscope conventionally has a cylindrical hand grip for housing a battery-powered, electric light source together with a thumb rheostat for controlling the intensity of illumination. An optical head carried atop the hand grip houses an optical system mounted between anterior and posterior sight holes. Light directed upward from a miniature electric lamp or coiled filament in the handle passes through a convex condensing lens and a reflecting prism or mirror, and thence through the anterior sight hole into an eye of the subject. The reflecting prism or mirror is mounted such that the upper extremity thereof covers only the lower portion of the sight holes, thereby permitting light reflected from an eye of the subject through the anterior sight hole to proceed on through an optical disk mounted behind the prism or mirror and on through the posterior sight hole.

Used in the direct modality, while holding the instrument in his right hand in a darkened room and with the light source activated, the observer positions the optical head as close as possible to the right eye of a seated subject, rotates the optical disk to select an appropriate magnifying loupe to neutralize his own and his subject's refractive error, and views the interior of the subject's right eye by peering through the sight holes with his right eye. Thereafter, the observer places the instrument in his left hand and with his left eye similarly examines the interior of the subject's left eye. By selecting a series of progressively lower diopter magnifying loupes, from +20 to +4 diopters for example, the observer can view interior structures in each of the eyes of the subject, progressing from the cornea, through the iris, lens, and vitreous to the ocular fundus, which appear to the observer as true and erect images in the direct modality and magnified up to fifteen times. In the indirect modality, however, the observer, positioned some distance away from the subject, holds the instrument in one hand close to his own eye, interposes a convex, condensing lens held in his other hand between the instrument and the subject, and, with a +2 or +4 diopter lens in the viewing aperture to neutralize his own accommodation, views an inverted, virtual image of the structures of the eye magnified up to four times. Indirect ophthalmoscopy has two significant advantages over direct ophthalmoscopy: It provides a large field of vision that gives the observer a good view of the ocular fundus even through an undilated pupil and in spite of opacities in the media, and it is not affected by major refractive errors in the subject's eyes. The disadvantages are the lower magnification and the inverted image.

The binocular indirect ophthalmoscope, which began to come into wide use in the 1950s, conventionally includes a head mount unit and external a.c. electric power source. The head mount unit houses an electric illumination source, which directs a focused light beam toward the object of regard, and a binocular optical system. The binocular optical system includes beam splitting elements to split light reflected from an object along a viewing axis into left and right optical paths. The reflected light thereafter passes through left and right eye pieces having a power of +1.00 to +1.25 diopters. The focused light source is usually mounted centrally and above the viewing axis, and powered from a wall mounted a.c. transformer and an electric cable. The beam splitting elements typically include two sets of parallel mirrors oriented at a 45 degree angle with respect to the viewing axis to optically reduce the interpupillary distance, which permits the observer to view with both eyes through a single anterior sight hole. A harness is attached to the head mount unit for mounting the unit to the head of the observer with the eye pieces positioned in front of the eyes of the observer. When used with a condensing lens, usually of +12 to +30 diopters and held at arms length, the observer can view an inverted, virtual image of the interior of an eye binocularly and with stereopsis. The magnification can be increased or decreased by changing the power of the condensing lens.

Despite the advantages of stereopsis, the head mounted binocular ophthalmoscope has several shortcomings. The focused light beam is not on the visual axis and only partially illumines the object of regard. A blind spot typically occurs. It can only be used in the indirect modality, which affords just an inverted, virtual image under relatively low magnification. Therefore, its use is ordinarily followed by switching to a monocular direct ophthalmoscope for more detailed viewing under higher magnifications. The instrument permits only a single viewing distance, which depends on the power of the eyepiece lens. If the observer moves closer to the condensing lens, the illumination axis deviates further away from the line of sight. If the observer moves farther away from the condensing lens, the deviation is reduced, but the ability of the examiner to do that is limited by the length of his arm. The mobility of the observer is limited by the attached, wall-mounted external power supply. Some persons find a head mounted unit uncomfortable and that wearing it may muss up a hairstyle.

To overcome these deficiencies, what is required is a portable, hand-held, battery-powered, binocular direct ophthalmoscope in which the illumination axis and the viewing axis are coaxial. Ideally, such an instrument would provide a true and erect binocular image with stereopsis under direct view and user-selectable magnification, variable between high and low under indirect view. Preferably, the handle of the instrument should be easily movable from a right side to a left side of the instrument for viewing the left eye and right eye of a subject, respectively, and vice-versa.

Berry, U.S. Pat. No. 4,836,166, disclosed a head-mountable instrument for illuminated stereoscopic viewing of body cavities. Berry's instrument included a centrally and anteriorly mounted light source that directed a light beam toward an inclined, one-way mirror, from which mirror the source beam was reflected forwardly along an illumination axis toward the object of regard. Light reflected back from the object along a viewing axis passed through the one-way mirror and was split into left and right optical paths by a pair of juxtaposed, back-to-back prisms, centrally disposed over the nose of the examiner. Light following the left and right optical paths was reflected posteriorly into the left and right eyes of the examiner, respectively, by left and right prisms disposed laterally and horizontally with respect to the central pair of prisms. This arrangement did make the illumination axis coaxial with the viewing axis, but placing a one-way mirror within the path of the reflected light tended to produce an unacceptably dim image.

LeVantine, U.S. Pat. No. 3,984,157, disclosed an improved monocular ophthalmoscope that incorporated beam splitting optics to make the viewing axis coaxial with the illumination axis, and further incorporated a light trap for absorbing substantially all of the light not utilized for illuminating the retina of the eye of a subject.

Clark et al., U.S. Pat. No. 5,078,469, disclosed a head-mountable binocular optical system comprising left and right loupes for magnified stereoscopic viewing and illumination during surgical procedures. Each loupe included a beam splitting optical cube having a beam splitting interface. Optical fibers supplied direct illumination to each loupe from a light source through a lens system and circular polarizing filter for reflection from the beam splitting interface outward through an objective lens along an illumination axis to illuminate a field of view. Light reflected from the field of view along a viewing axis passed through the objective lens to the optical interface where it was transmitted, in part, to a circular polarizing filter and a Pechan/Schmidt roof prism on through eyepiece optics and into an eye of an observer. Thus, the illumination axis and the viewing axis were coaxial, and the polarizing filters reduced the flare effect that otherwise occurs with high intensity illumination.

There remains, however, a need for a portable, hand-held, binocular direct ophthalmoscope that overcomes the above-noted deficiencies of the binocular indirect ophthalmoscope, that dispenses with the need for a monocular ophthalmoscope, and that can also be used in the indirect modality.

OBJECTS OF THE INVENTION

It is an object of the present invention to provide a portable, hand-held, binocular direct ophthalmoscope equipped with a battery-powered light source.

Another object of the present invention is to provide such an instrument for which the illumination axis is coaxial with the viewing axis.

A further object of the present invention is to provide such an instrument that permits the observer, using one hand only, to simultaneously interpose magnifying lenses of successively varying powers before each of his own eyes.

A still further object of the present invention is to provide such an instrument with a handle that can be easily moved back and forth between the right and left sides of the instrument in order to facilitate close up viewing of the left and right eyes of a subject, respectively.

An additional object of the present invention is provide such an instrument that can also be used in the indirect modality.

Another object of the present invention is to provide such an instrument in which the interpupillary distance is adjustable.

Other objects, advantages and details of the invention will be explained hereinafter and more fully delineated in the appended claims.

SUMMARY OF THE INVENTION

In order to accomplish the above and other objects, the binocular direct ophthalmoscope in accordance with the present invention comprises light beam generating means for projecting a focused beam of light along a first, i.e, illumination, axis to a patient's eye, a binocular optical system for splitting light reflected from the patient's eye into left and right optical paths for transmission through observer-selectable magnifying lenses and into the eyes of a viewer, and hand-held support means for supporting the light beam generating means and the binocular optical system. The light beam generating means includes a light source and means for deflecting the light from the light source along the illumination axis. In a preferred embodiment, the hand-held support means includes a cylindrical handle, a laterally-extended support beam having a first end rigidly attached to the handle and an opposite free end, and a frame rotatably suspended from the free end of the support beam. This arrangement permits easy movement of the handle between the left and the right sides of the instrument. The handle is adapted for receiving and storing electric storage batteries, and equipped with a combination thumb rheostat-on/off switch for controlling and powering the light source in the manner that is conventional in monocular ophthalmoscopes.

The binocular optical system is housed and supported by the frame, and includes beam splitter means positioned on the illumination axis for receiving and splitting a portion of the reflected light into a left-directed beam and a right-directed beam; left beam deflecting means for deflecting light from the left-deflected beam along a second axis toward the left eye of an observer; right beam deflecting means for deflecting light from the right-deflected beam along a third axis toward the right eye of an observer; and means for simultaneously positioning any one of a plurality of observer-selectable magnifying loupes on the second and third axes, respectively. The light source and the means for deflecting light are disposed within the beam splitter means and substantially coplanar therewith. The light that is split by the beam splitter means lies within a circle normal to the illumination axis of diameter not exceeding 8 mm.

In a preferred embodiment, the beam splitter means comprises a beam splitter block mounted to the frame and having left and right front surfaces, which front surfaces are symmetrically and obliquely disposed on opposite sides of the illumination axis, thereby defining a V-shape surface in top planar view. The block has a recessed cavity for receiving and mounting a miniature light bulb connected by electric cables to the storage batteries. A light source aperture is aligned on the illumination axis and cut through the front surfaces of the block to the cavity. Left and right beam splitter mirrors are attached to the left and right front surfaces of the beam splitter mirrors, respectively, and each has a notch cut away adjacent the illumination axis to permit light from the light source to exit the block between the beam splitter mirrors.

In a preferred embodiment, the left and right beam deflecting means are left and right mirrors mounted to the frame on opposite sides of the illumination axis positioned to receive left and right deflected beams, respectively, and to reflect them rearward along second and third axes through left and right dioptric disk assemblies, respectively. The dioptric disk assemblies permit the examiner to interpose any one of a plurality of magnifying loupes into the second and third axes immediately in front of the observer's left and right eyes, respectively.

Laterally adjustable means are provided for mounting the dioptric disk assemblies to the frame which, in a first embodiment of the invention, comprise a C-channel attached to the frame and left and right dioptric disk assembly mounts adapted for sliding movement within the C-channel, whereby the distance between dioptric disk assemblies attached to the mounts can be adjusted. In a second, alternative embodiment of the invention, each disk assembly is provided with a lens power knob for rotating a worm gear around a fourth axis in mating engagement with a matching spur gear attached to the disk assembly, such that rotation of a lens power knob sequentially rotates into the field of view magnifying loupes of various magnifying powers distributed around the periphery of the lens disk. Oppositely-directed left and right connecting shafts are provided that are connected to the right and left worm gears, respectively, for rotation therewith, the connecting shafts being aligned along the fourth axis and mutually engaged in telescopic relation.

In a third, alternative embodiment, an idler gear is interposed between the disk assemblies and mounted to the frame for rotation about a fifth axis parallel to the illumination axis. A circular array of radial teeth are attached to the periphery of each disk assembly and meshed for driving engagement with the teeth of the idler gear, and means are attached to the frame for mounting the left and right disk assemblies for counter-rotational displacement about the fifth axis and for rotation about sixth and seventh axes respectively. Accordingly, in the third embodiment, rotation of either disk assembly in a first direction causes rotation of the other disk assembly in a second, opposite direction, and partial semi-circular displacement of each assembly about the fifth axis permits adjusting the ophthalmoscope to accommodate the interpupillary distance of the examiner.

Figure 5:
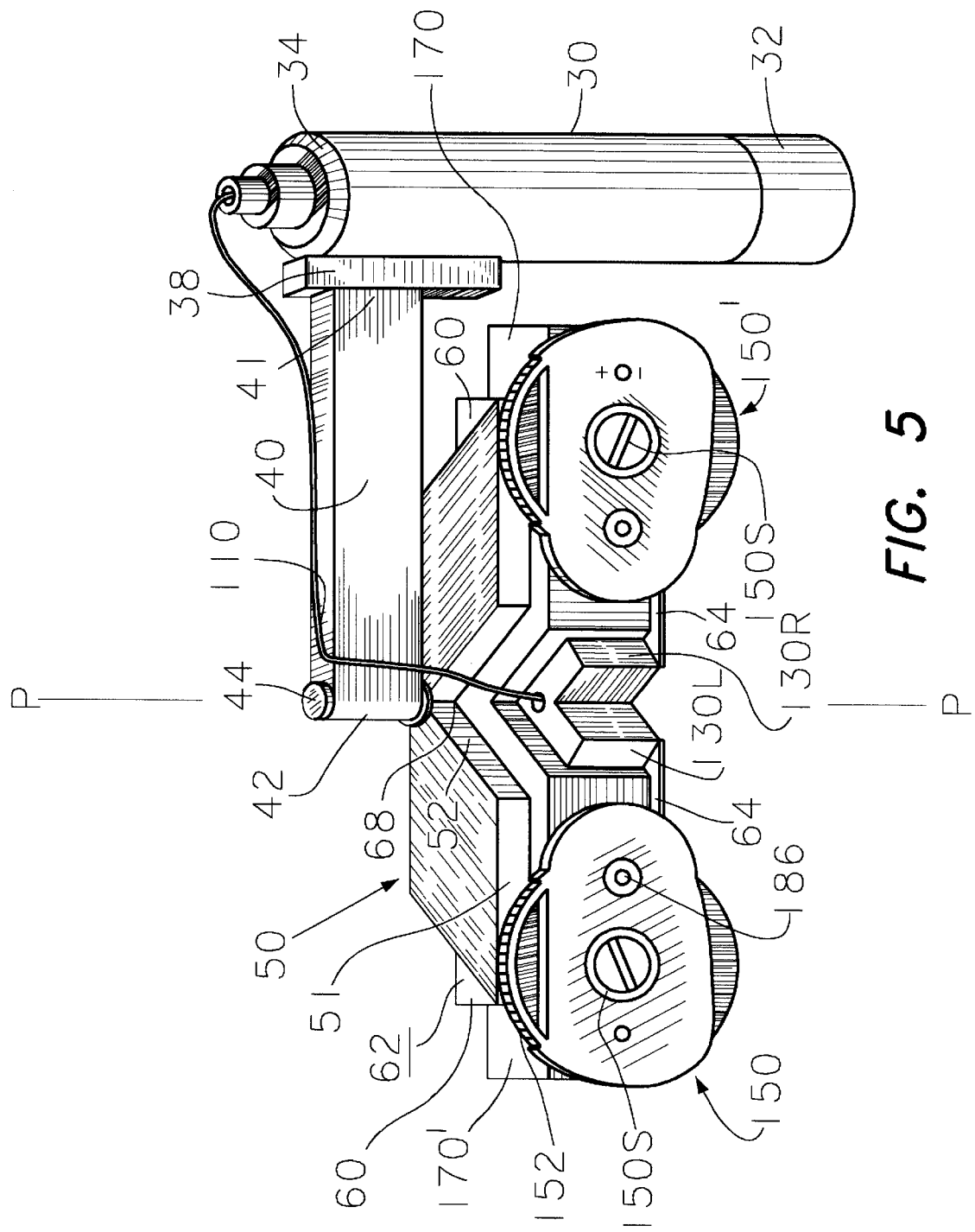
FIG. 5 is a perspective view of a first embodiment of the present invention as seen from the rear and above and with the handle positioned on the right side of the frame thereof.

The terms "left," "right," "forward," and "rear" shall be understood throughout as referring to the present invention as shown oriented in FIG. 5.

DETAILED DESCRIPTION OF THE PREFERRED EMBODIMENTS

Figure 1:
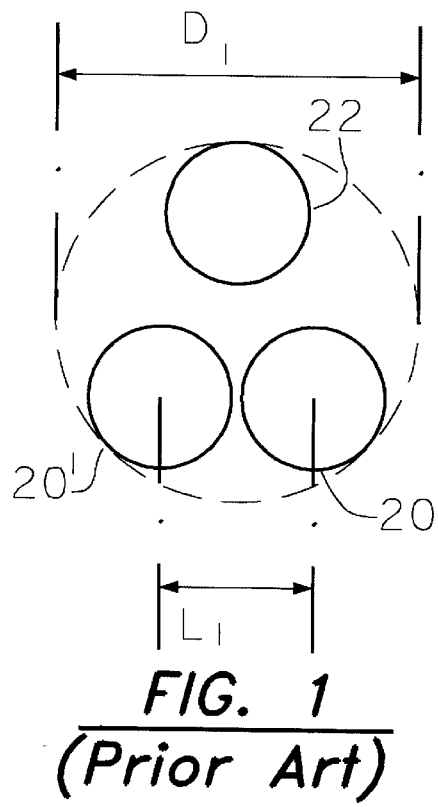
FIG. 1 is a schematic diagram showing in enlarged, frontal elevation the positions of left and right viewing apertures and illumination source exit aperture in a binocular indirect ophthalmoscope of the prior art.
Figure 2:
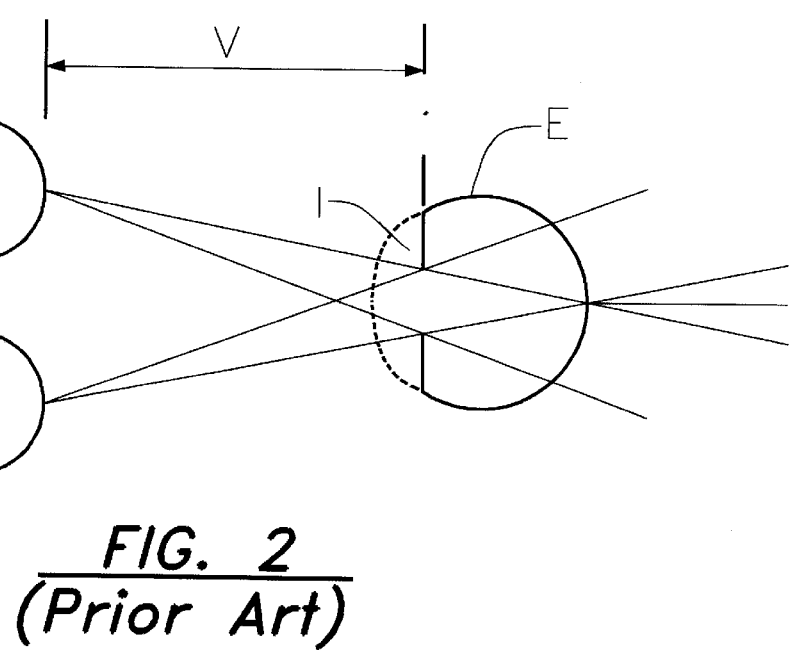
FIG. 2 is a schematic diagram in top plan view of the same in direct modality and showing the optical paths of light reflected from the eye of a subject toward the left and right viewing apertures, resulting in diplopia.

If one attempts to use a binocular indirect ophthalmoscope, as such have been known in the prior art, in the direct modality to view an eye of a subject, it is impossible to achieve stereopsis. Referring to FIG. 1, it may be seen that horizontally adjacent left and right viewing apertures 20, 20' for such an ophthalmoscope, the Topcon Model ID-5 for example, together with an overlying illumination source exit aperture 22, are all positioned within a circle having diameter $D_1$=35 mm. The distance $L_1$ between the left and right viewing apertures is 22 mm. As shown in FIG. 2, when such an ophthalmoscope is placed a distance V equal to 30 mm, more or less, from the eye E of a subject, due to the relatively wide distance $L_1$, the optical paths of rays reflected through the iris I toward the viewing apertures 20, 20' transmit nonoverlapping images, resulting in diplopia instead of stereopsis.

Figure 3:
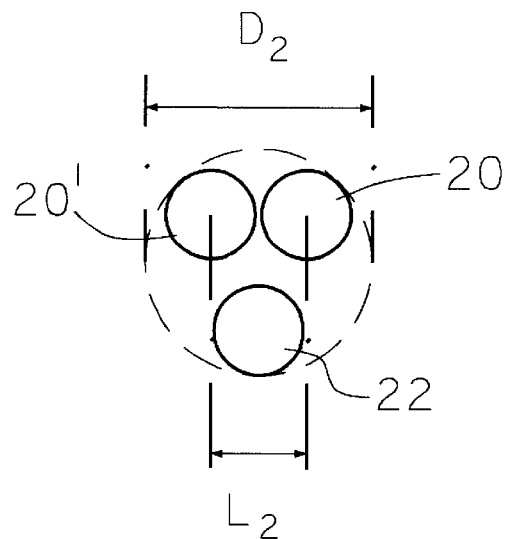
FIG. 3 is a schematic diagram in enlarged, front elevational view showing the positions of the left and right viewing apertures and illumination source exit aperture in the present invention.
Figure 4:
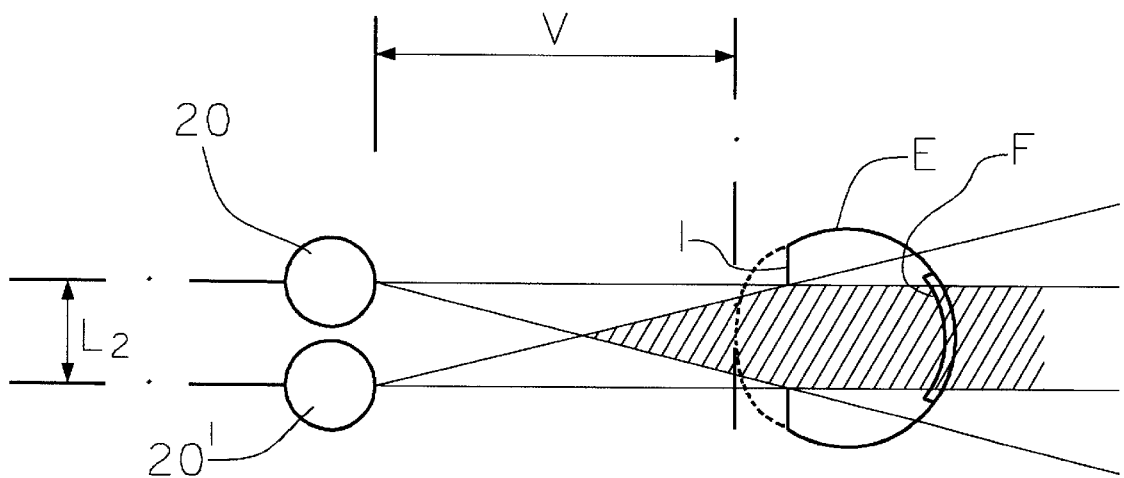
FIG. 4 is a schematic diagram in top plan view of the same in direct modality and showing the optical paths of light reflected from the eye of a subject, resulting in stereopsis.

Referring now to FIG. 3, in the present invention horizontally adjacent left and right viewing apertures 20, 20' and an illumination source aperture 22 all lie within a circle of diameter $D_2$ equal to 6 or 7 mm and the distance $L_2$ between the viewing apertures is only 3 mm. As shown in FIG. 4, the narrow distance $L_2$ between the viewing apertures, which approximates the width of the iris I, permits stereoscopic viewing throughout the depth of the eye E (shown by hatching) as far back as the ocular fundus, F.

Figure 6:
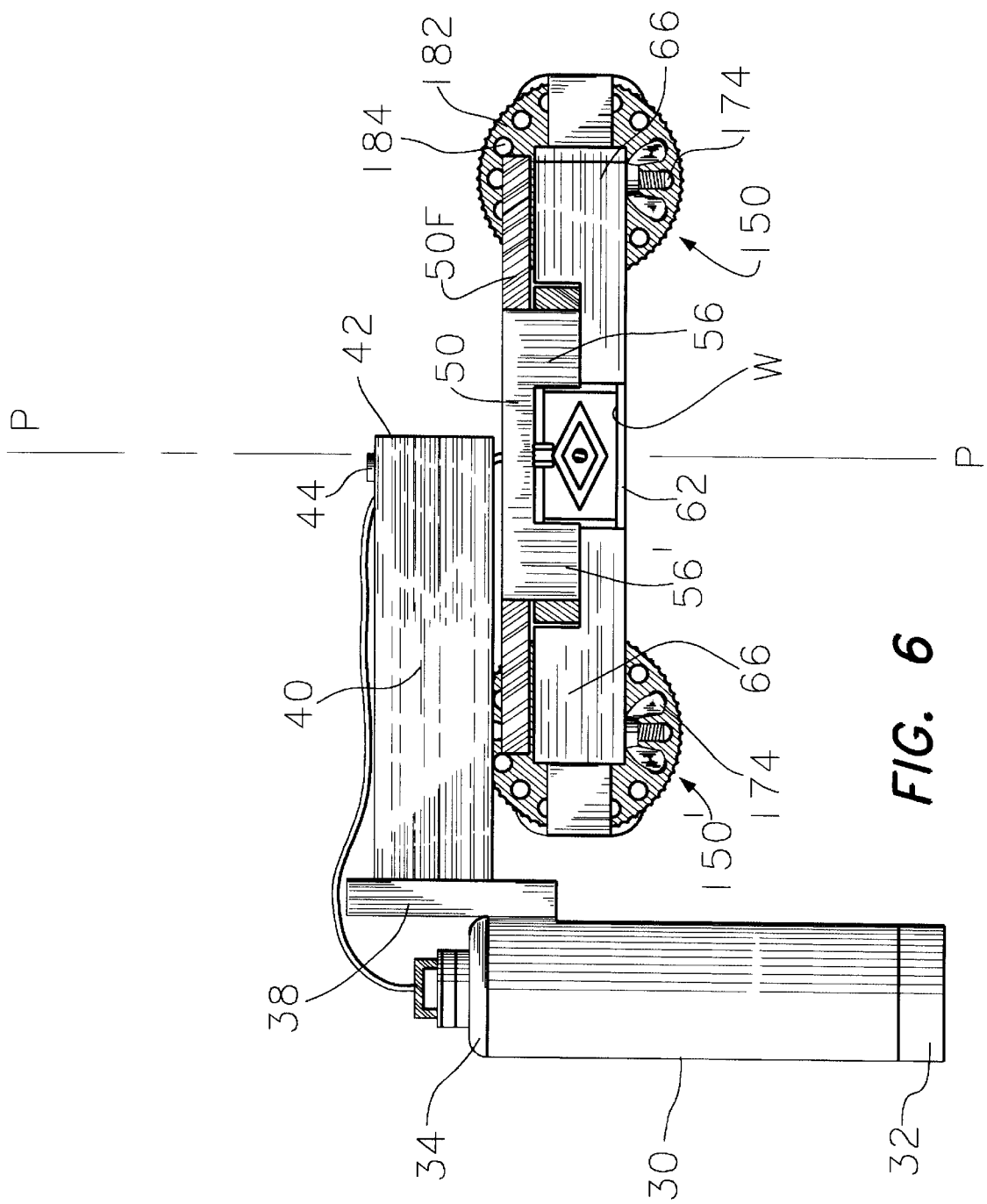
FIG. 6 is a front, elevational view of the same.

FIG. 5 shows a first embodiment of the present invention in rear perspective view. A handle 30 comprises a hollow cylinder that houses one or more dry cell batteries (not shown), closed at a bottom end by screw cap 32. A thumb-operated, combination rotary rheostat 34 and on/off switch connected in series with the batteries is mounted at an upper end of the handle 30. A vertical stanchion 38 is rigidly attached to a left side of the cylinder 30. A horizontally-elongated support beam 40 has a right end 41 rigidly attached to the stanchion 38 and a free left end 42. A chevron-shaped frame 50, having a centrally-disposed, first V-notch 52 cut away from a rear margin 51 thereof, is pivotally suspended on pivot axis P—P by pivot pin 44 inserted through a first vertical bore (not shown) in the free end 42 and through a second vertical bore (not shown) through the frame 50 just forward of the V-notch 52. A horizontally-elongated C-channel 60 is fixed to an underside 50U of the frame 50 and comprises a top wall 62, bottom wall 64 and front wall 66, as may best be seen in FIGS. 6 and 7. Left and right flanges 56, 56' of the frame 50 project partially downward from a front wall 50F thereof, adjacent the front wall 66 of the channel 60. The flanges 56, 56', together with a rectangular opening cut away from the front wall 66, define a forward-facing, rectangular window W symmetrically disposed about the vertical pivot axis P—P and about the horizontal illumination axis I—I.

The top wall 62 of the C-channel 60 is also cut away to form a second V-notch 68 symmetrically disposed about the pivot axis P—P and the illumination axis I—I, the vertex of the notch 68 being adjacent the front wall 66. Both the first notch 52 and the second notch 68 include a total of 90 degrees of angle, bifurcated by a plane defined by the axis P—P and I—I (the "I-P plane") into two equal 45 degree angles.

Figure 8:
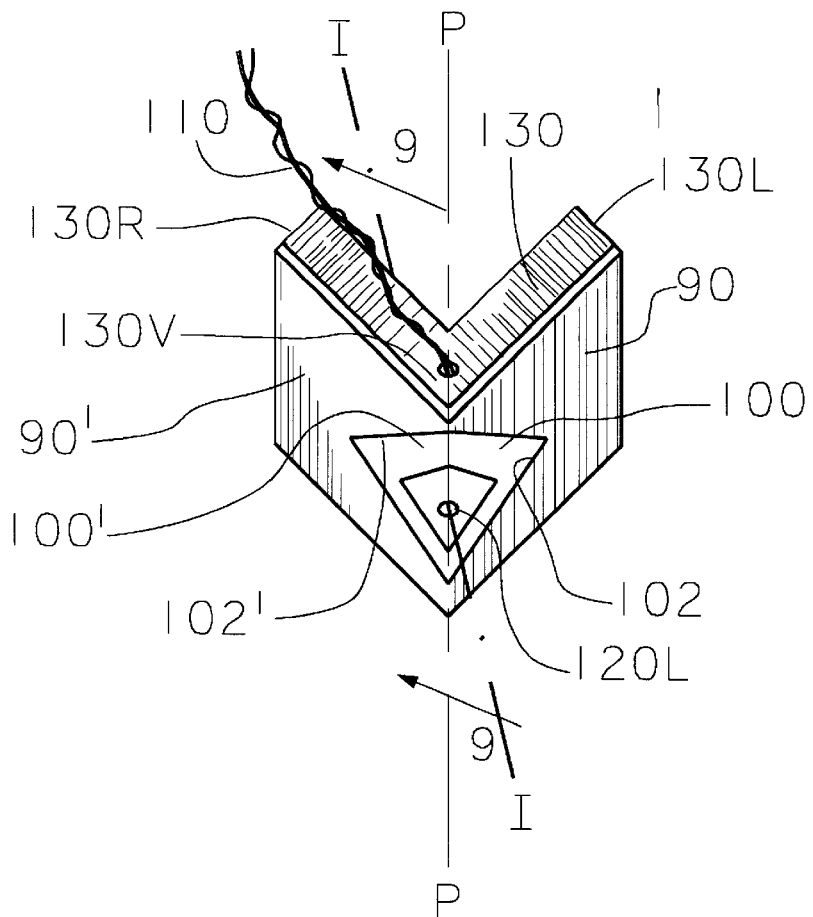
FIG. 8 is an enlarged, perspective view of the beam splitter mounting block thereof.

Referring to FIGS. 5 and 8, vertical left and right mirror support plates 90, 90' line the second notch 68 and extend from the bottom wall 64 to the top wall 62. Forward-facing beam splitting mirrors 100, 100' are attached to front surfaces of each of the plates 90, 90', and forward, apical portions of said mirrors 100, 100' are exposed to incident light by third V-notches 102, 102' cut out of the plates 90, 90'.

Figure 9:
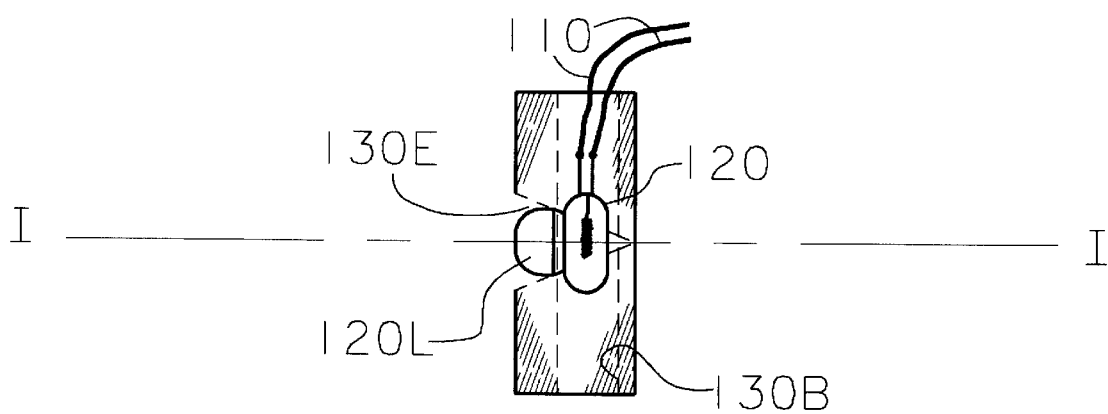
FIG. 9 is a cross-sectional view thereof taken along line 9—9 of FIG. 8.

Referring to FIGS. 8 and 9, the mirrors 100, 100' are mounted on front surfaces of a beam splitter block 130 comprised of left and right vertical, parallelepiped portions 130L, 130R joined at a 90 degree vertex 130V, which vertex, like the first and second V-notches 52, 68, is bisected by the I-P plane. The vertex 130V has a vertical bore 130B into which is inserted a miniature halogen bulb 120 connected by electric cables 110 to dry cell batteries in the handle 30, which serves as an illumination source. An illumination source exit aperture 130E comprises third and fourth V-notches 140, 140' cut away from left and right mirrors 100, 100,'and the underlying portions of the block 130, respectively, to permit light emitted by the bulb 120 to travel forward through a convex focusing lens 120L and thence along the illumination axis I—I toward the eye of a subject. By keeping the illumination source 22 comprising the bulb 120 and lens 120L, and the mirrors 100, 100' within a 6 to 7 mm diameter circle about the illumination axis, the illumination axis is substantially collinear with the viewing axis; compare FIGS. 3, 4, 8 and 9.

Figure 7:
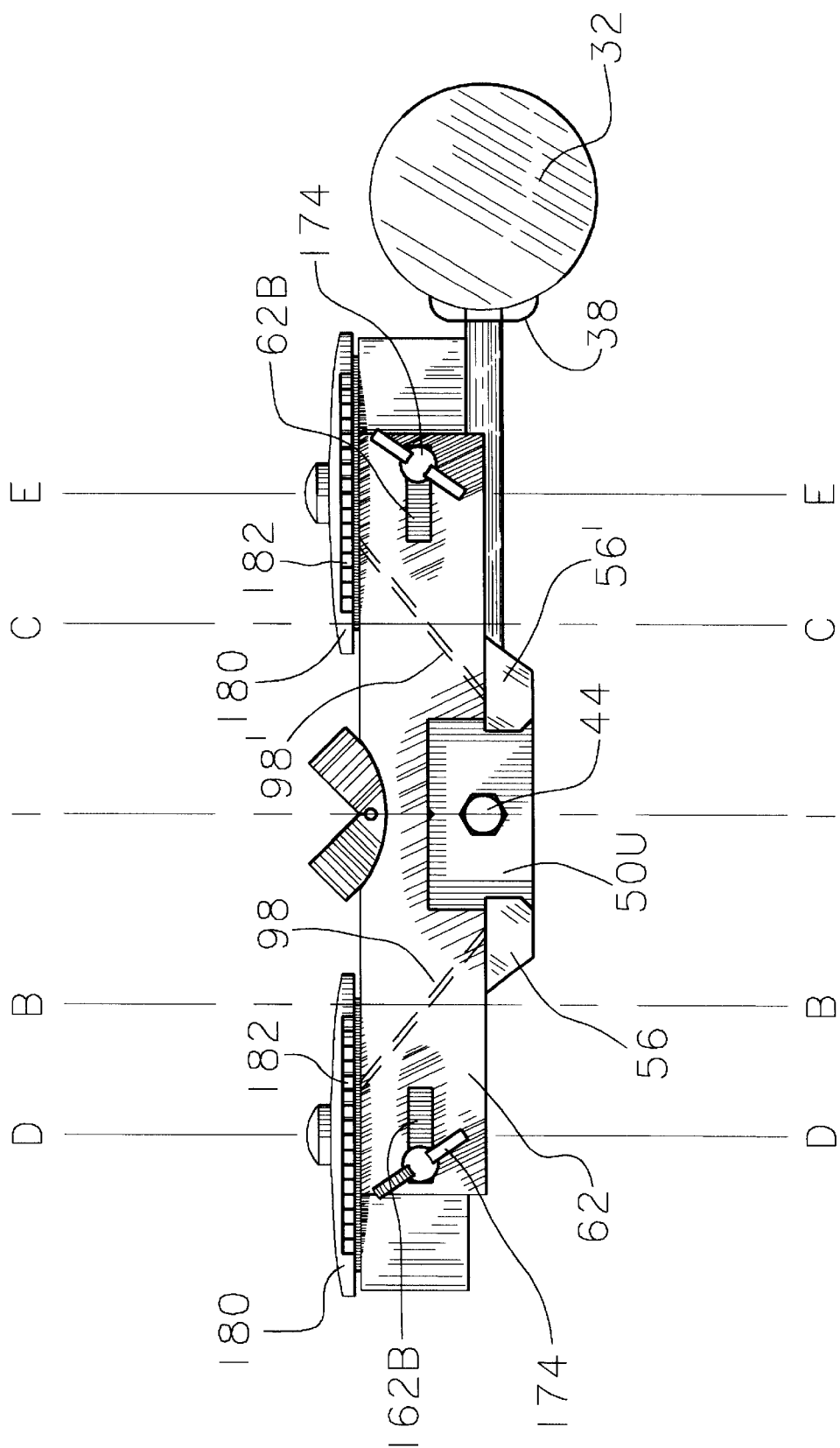
FIG. 7 is a bottom view of the same.
Figure 10:
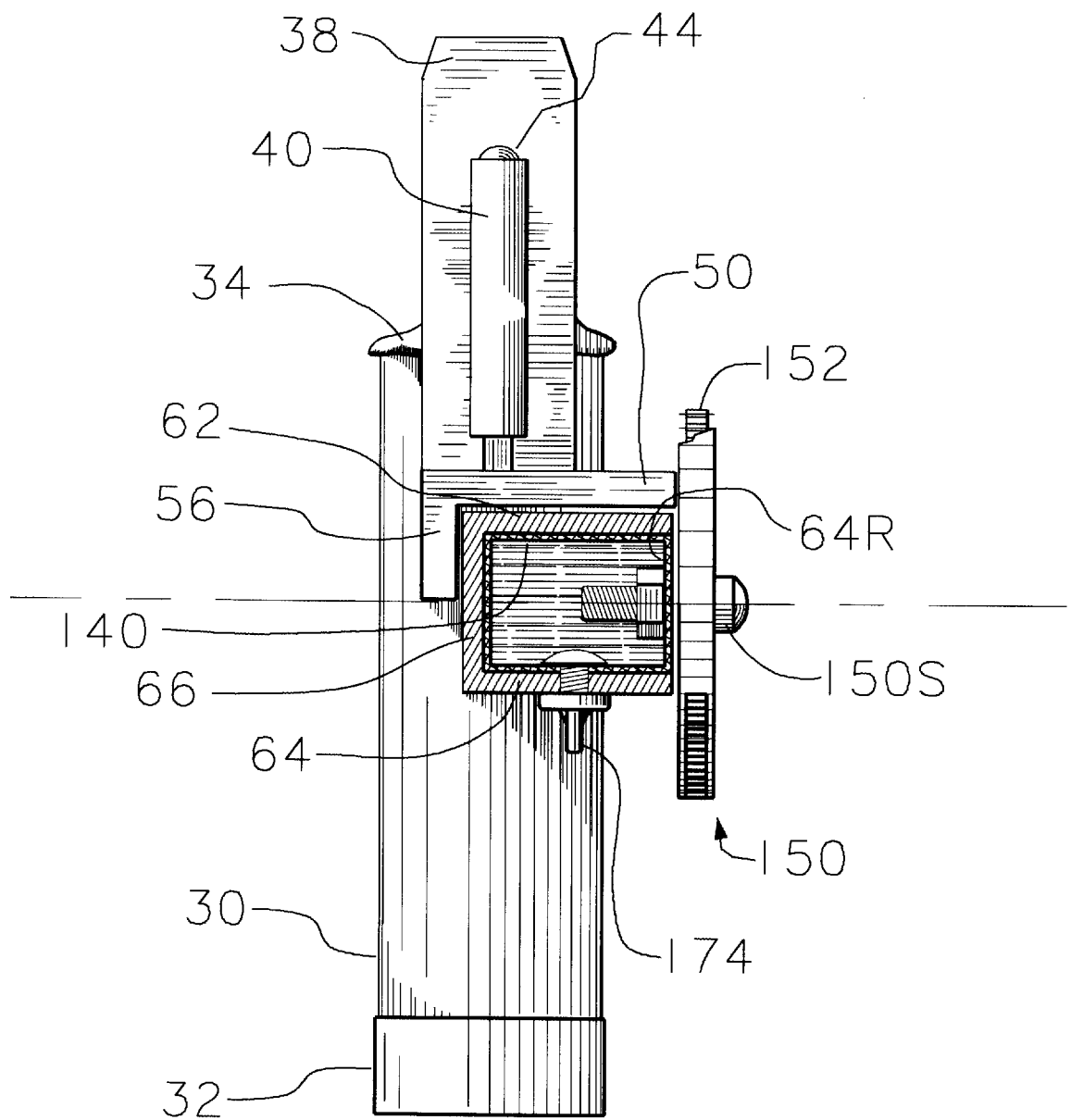
FIG. 10 is a left side view thereof.

The first embodiment of the invention further includes left and right dioptric disk assemblies, denoted generally by the numerals 150, 150', which are mounted for lateral sliding adjustment along the C-channel 60. For this purpose, left and right dioptric disk assembly mounts 170, 170' are provided, being laterally elongated channels of rectilinear cross-section adapted to fit and slide smoothly within the C-channel 60, as shown, for example, in FIGS. 5 and 10. To a rear wall 64R of each mount 170, 170' is attached a dioptric disk assembly 150, 150' by threaded fasteners 150S, respectively. As shown in FIG. 7, a pair of oppositely-directed slots 62B, 62B' in the bottom wall 64 of the C-channel 60 extend from the left and right ends thereof, respectively, and threaded bolts with wing nuts 174 extend therethrough and through bores in the bottom walls of the mounts 170, 170', thereby permitting lateral sliding adjustment of the positions of the dioptric disk assemblies 150, 150'. The left and right dioptric disk assemblies 150, 150' each include a housing 180 upon which a dioptric disk 182 is mounted for rotation about horizontal axes D—D and E—E, respectively, and a viewing aperture 186. The dioptric disks 182 each have a series of magnifying loupes 184 of differing magnifying powers distributed around the periphery thereof. Left and right deflection mirrors 98, 98' are mounted within the C-channel, laterally spaced apart on opposite sides of the beam splitting mirrors 100, 100', and angled obliquely with respect to the I-P plane. Light incident on the beam splitting mirrors 100, 100' is reflected into a left-directed path and right-directed path, which respective light beam paths are deflected rearward by reflection off the deflection mirrors 98, 98' along second axis B—B and a third axis C—C, respectively, thence through a magnifying loupe 184 of a dioptric disk 182 and further rearward through a viewing aperture 186 into an eye of an observer.

Figure 11:
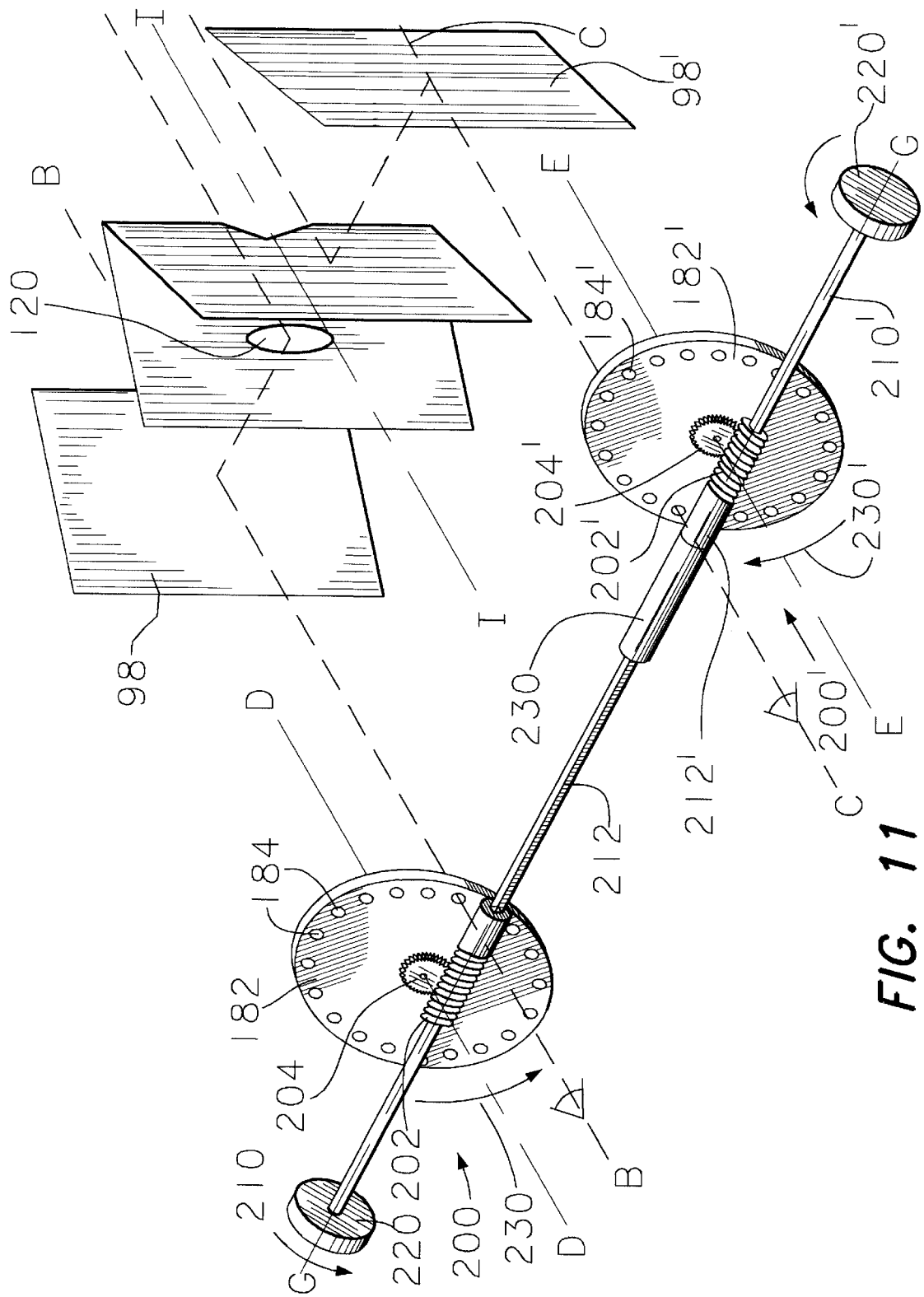
FIG. 11 is an enlarged, schematic diagram of a second, alternative embodiment of the invention utilizing worm gear assemblies to rotate right and left dioptric disks.
Figure 12:
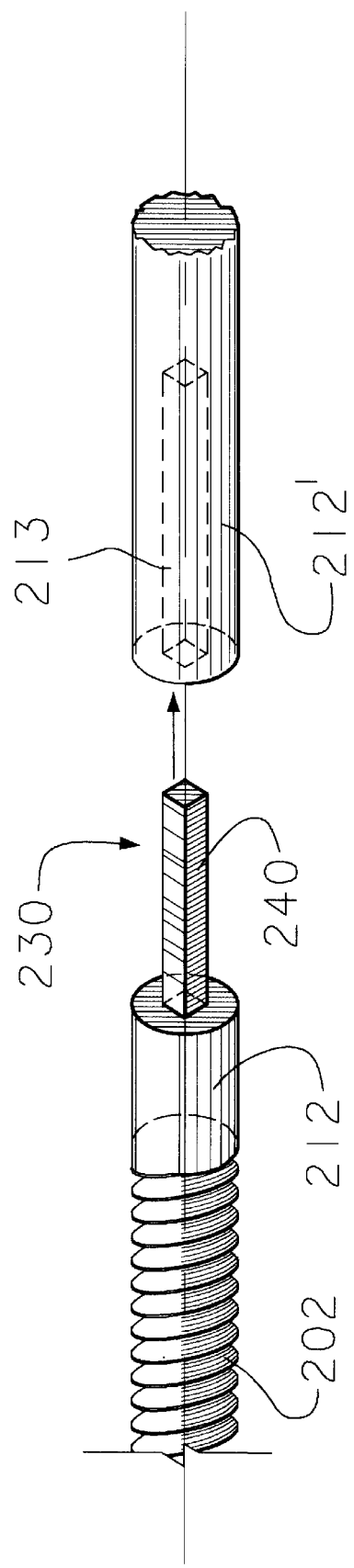
FIG. 12 is an enlarged, exploded view of telescoping shafts thereof.

An alternative embodiment of the invention is illustrated schematically in FIG. 11, wherein left and right worm gear drive assemblies, denoted generally by the numerals 200, 200', are provided for each of the left and right dioptric disk assemblies 150, 150'. The left and right worm gear drive assemblies 200, 200' comprise left and right worm gears 202, 202' aligned on a horizontal axis G—G parallel to, and to the rear of, the frame 50, and matching left and right spur gears 204, 204' attached to a rear, central portion of the left and right dioptric disks, and in meshed engagement with said spur gears 202, 202', respectively. Right and left lens power knobs 220, 200' are connected to the worm gears 202, 202', by distal connecting shafts 210, 210' for rotation therewith. Left and right medial connecting shafts 212, 212' connect the spur gears 202, 202' with each other through a telescopic coupling 230 that permits lateral movement of the worm gear assemblies 200, 200' and associated dioptric disks 182, 182' toward and away from each other to adjust for the interpupillary distance of the observer. Thus, rotation of either lens power knob will cause both dioptric disks 182, 182' to rotate simultaneously in order to bring a selected magnifying loupe 184 onto axes B—B and C—C, respectively. Preferably, the left and right spur gears 182, 182' have opposite thread orientations so that rotation of either lens power knob 220, 220' causes the dioptric disks 182, 182' to rotate in opposite directions about horizontal axes D—D and E—E, as shown by the arrows 230, 230', respectively. As shown in FIG. 12, the telescopic coupling 230 preferably includes a shank 240 of square cross-section extending medially from the left connecting shaft and a distally-extending recess 213 of mating square cross-section in the right connecting shaft 212' for receiving said shank 240. Accordingly, this alternative embodiment likewise permits adjusting the interpupillary distance to suit the observer.

Figure 13:
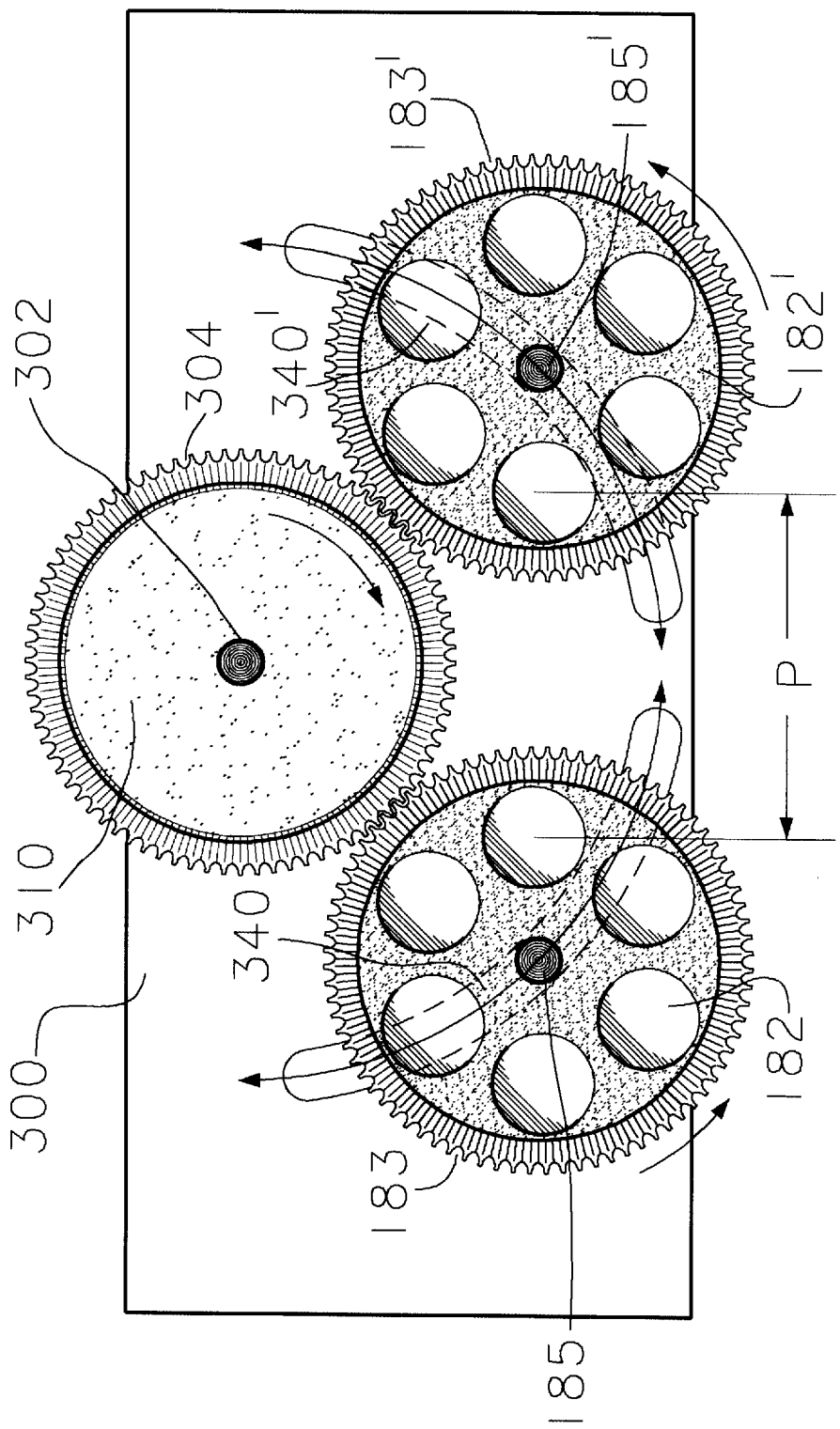
FIG. 13 is a rear, elevational view of a dioptric disk and idler gear drive assembly of a third, alternative embodiment of the invention.

FIG. 13 illustrates a third alternative embodiment that provides a vertical mounting plate 300 for attachment to the frame 50. An idler gear 310 is mounted to the plate 300 for rotation about a horizontal axis F—F (not shown) by idler gear shaft 302. Left and right dioptric disks 182, 182' are mounted to the plate 300 for rotation about horizontal axes D—D and E—E (not shown) by dioptric disk shafts 185, 185'. Each of the dioptric disks 182, 182' is provided with a plurality of radial teeth 183, 183' on the periphery thereof, in driving engagement with the teeth 304 of the idler gear. The left and right dioptric disk shafts 185, 185' are inserted through left and right arcuate slots 340, 340' having constant radial distance from axis F—F, said slots 340, 340' being symmetrically disposed on opposite sides of a vertical plane that includes axis F—F. Rotation of the idler gear 310 will cause simultaneous rotation of both dioptric disks 182, 182'. Reversible means are provided for fixing the left and right dioptric disk shafts 185, 185' at a position anywhere within said slots 340, 340', respectively, to select a suitable interpupillary distance.

Figure 14A:
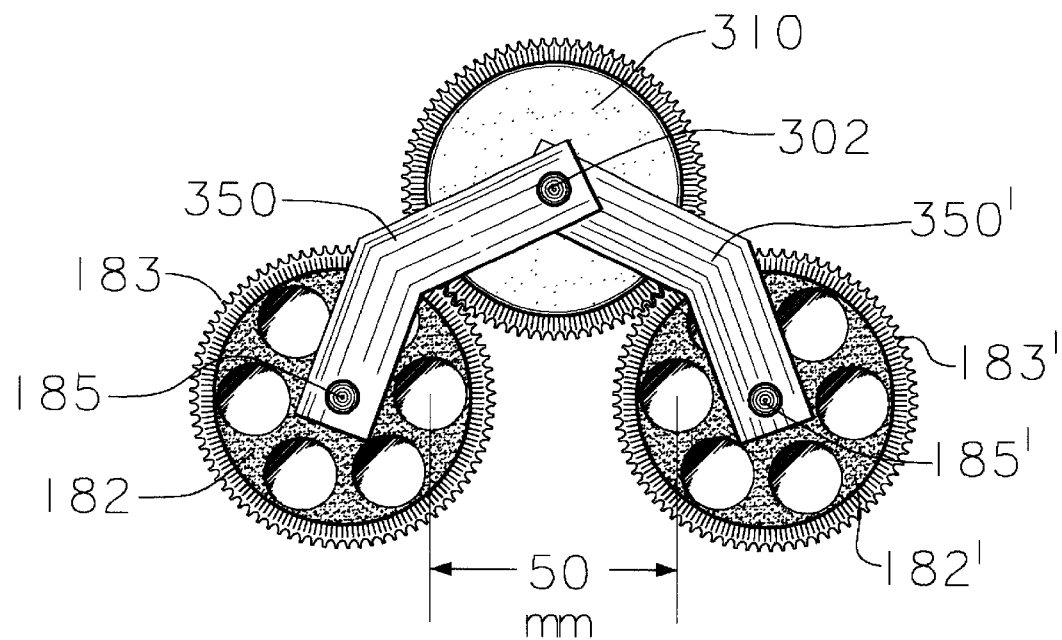
FIG. 14(a) is a variation on the dioptric disk and idler gear drive assembly of FIG. 13, adjusted for a desired minimum interpupillary distance.
Figure 14B:
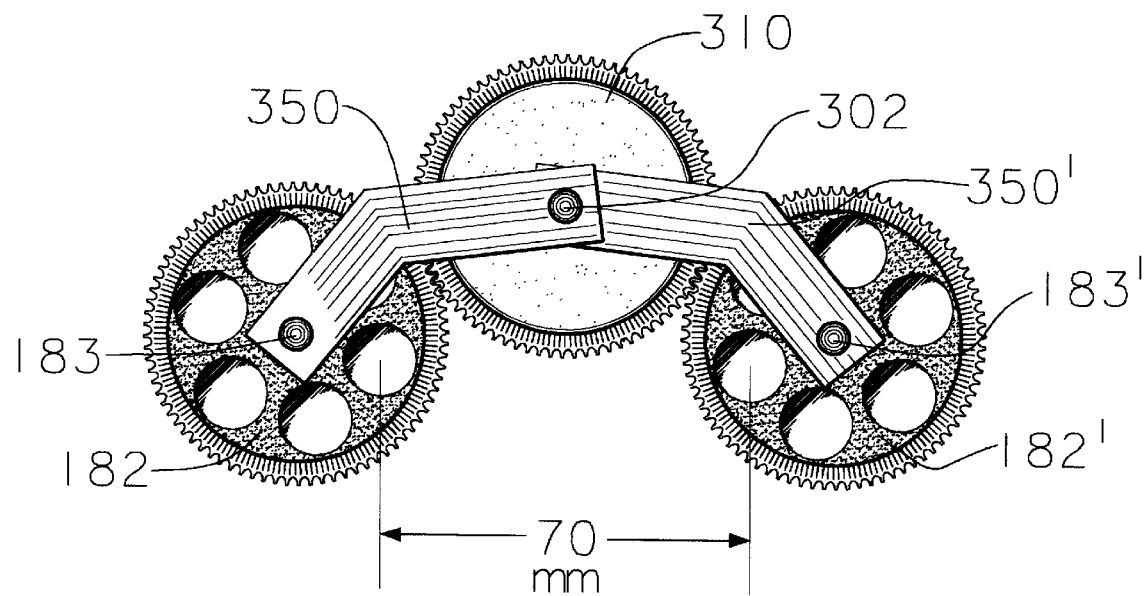
FIG. 14(b) is the same variation adjusted for a desired maximum interpupillary distance.

In another variation, the vertical mounting plate 300 is dispensed with, and instead left and right arms 350, 350' are provided, each of the arms having one end pivotably mounted on the idler gear shaft 302 and an opposite end pivotably mounted on the left and right dioptric disk shafts 185, 185', respectively, as shown in FIG. 14(*a*), (*b*). The desired range of interpupillary adjustment is between 50 mm, as shown in FIG. 14(*a*), and 70 mm, as shown in FIG. 14(*b*). In this variation, the dioptric disk shafts 185, 185' may be inserted through a laterally-extended slot (not shown) in a front wall 66 of the C-channel 60, such that lateral displacements of the dioptric disks 182, 182' correspond to vertical displacements of the idler gear 310.

Various changes and modifications will become obvious to those skilled in the art. It is the intent that these changes and modifications are to be encompassed within the spirit of the appended claims and that the invention described herein and shown in the accompanying drawings are illustrative only and are not intended to limit the scope of the invention.

I claim:

1. A hand held, binocular direct ophthalmoscope of the type in which the viewing axis is substantially coaxially-aligned with a beam of light directed into the eye under examination and equipped with a binocular optical assembly for stereoscopic viewing by an observer of light reflected from the eye, comprising:

(a) light beam generating means, including a light source for generating a beam of visible light along a first axis;

(b) a binocular optical system, including (1) beam splitter means positioned on said first axis for receiving and splitting a portion of the reflected light into a left-directed and a right-directed beam;

(2) left beam deflecting means for deflecting light from the left-directed beam along a second axis toward the left eye of the observer;

(3) right beam deflecting means for deflecting light from the right-directed beam along a third axis toward the right eye of the observer;

(4) means for simultaneously positioning any one of a plurality of observer-selectable magnifying loupes on the second and third axes, respectively; and (c) hand-held support means for supporting the light beam generating means and the binocular optical system; wherein the light source, the left beam deflecting means, and the right beam deflecting means are all disposed substantially within a single plane that includes the first, second and third axes, and wherein the portion of the reflected light that is split by the beam splitter means lies within a circle centered on and normal to the first axis and having a diameter of up to eight millimeters.

2. The ophthalmoscope of claim 1, wherein the hand-held support means comprises:

a handle;

a laterally-extended support beam having a first end rigidly attached to the handle and an opposite free end; and a frame rotatably suspended from the free end of the support beam and attached to the binocular optical system; whereby, in use, the observer can alternately rotate the handle from one side to an opposite side of the support beam.

3. The ophthalmoscope of claim 2, wherein the beam splitter means comprises:

a beam splitter block mounted to the frame and having left and right front surfaces, said front surfaces being symmetrically and obliquely disposed on opposite sides of the first axis, thereby defining a V-shape front surface in top planar view, said block having a recessed cavity for receiving and mounting the light source, and a light source aperture aligned on the first axis and cut through said front surfaces to said cavity; and left and right beam splitter mirrors mounted on said left and right front surfaces, respectively, each of said beam splitter mirrors having a notch cut away adjacent the first axis to permit light from the light source to exit the block between said beam splitter mirrors.

4. The ophthalmoscope of claim 3, wherein the left beam deflecting means is a left deflection mirror mounted to the frame and positioned for receiving and deflecting light from the left-deflected beam to the second axis, and the right beam deflecting means is a right deflection mirror mounted to the frame and positioned for receiving and deflecting light from the right-deflected beam to the third axis.

5. The ophthalmoscope of claim 4, wherein the left and right magnifying means is a left and right diopter disk assembly, respectively, and further comprising laterally-adjustable means for mounting the diopter disk assemblies to the frame.

6. The ophthalmoscope of claim 5, wherein the laterally-adjustable means for mounting the diopter disk assemblies to the frame comprises:

(a) left and right worm gears mounted to the frame for rotation about a fourth axis, said fourth axis being parallel to the frame;

(b) oppositely directed left and right connecting shafts attached to the left and right worm gears, respectively, for rotation therewith, said connecting shafts being aligned along the fourth axis and mutually engaged in telescopic relation;

(c) a lens power knob rigidly mounted to a free end of each worm gear; and (d) a left and a right spur gear centrally disposed on the left and right optical disk assemblies, respectively, for rotation therewith, and in mating engagement with the left and right worm gear drives, respectively;

whereby rotation of the left or right lens power knob simultaneously rotates both the left and right optical disk assemblies, and the distance between the second and third axes can be adjusted by lateral movement of the optical disk assemblies toward or away from one another in order to accommodate the interpupillary distance of the observer.

7. The ophthalmoscope of claim 6, wherein the laterally-adjustable means for mounting the diopter disk assemblies to the frame comprises:

(a) an idler gear interposed between the disk assemblies and mounted to the frame for rotation about a fifth axis parallel to the first axis;

(b) a circular array of radial teeth attached to the periphery of the diopter disk assemblies and meshed for driving engagement with the teeth of the idler gear; and (c) means attached to the frame for mounting the left and right dioptric disk assemblies for counter-rotational displacement about the fifth axis and for rotation about sixth and seventh axes, respectively;

whereby, rotation of either diopter disk assembly in a first direction causes rotation of the other diopter disk assembly in a second, opposite direction, and partial, counter-circular displacement of said assemblies about said fifth axis permits adjusting the ophthalmoscope to accommodate the interpupillary distance of the observer.

8. The binocular ophthalmoscope of claim 6, wherein the laterally-adjustable means for mounting the diopter disk assemblies to the frame comprises:

(a) an idler gear interposed between the disk assemblies for rotation on an idler gear shaft about a fifth axis parallel to the first axis;

(b) a circular array of radial teeth attached to the periphery of the diopter disk assemblies and meshed for driving engagement with the teeth of the idler gear; and (c) left and right arms, each arm having a first end pivotally attached to the idler gear shaft and a second, opposite end pivotally attached to the left and right diopter gear disk shafts for rotation about sixth and seventh axes, respectively;

whereby, rotation of either diopter disk assembly in a first direction causes rotation of the other diopter disk assembly in a second, opposite direction, and lateral displacements of the diopter disk assemblies for adjusting interpupillary distance corresponds to vertical displacements of the idler gear.

9. The binocular ophthalmoscope of claim 6, 7, or 8, wherein the handle is cylindrical, closed at a bottom end, and adapted for receiving and storing electric storage batteries for powering the light source.

* * * * *